US00PP23957P3

(12) United States Plant Patent
Whitcomb

(10) Patent No.: US PP23,957 P3
(45) Date of Patent: Oct. 8, 2013

(54) SUGAR MAPLE TREE NAMED 'WHIT XLV'

(50) Latin Name: ***Acer saccharum* var. *caddo***
Varietal Denomination: WHIT XLV

(75) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 97 days.

(21) Appl. No.: 13/134,759

(22) Filed: Jun. 15, 2011

(65) Prior Publication Data

US 2012/0324609 P1 Dec. 20, 2012

(51) Int. Cl.
*A01H 5/00* (2006.01)

(52) U.S. Cl.
USPC ..... Plt./224

(58) Field of Classification Search
USPC ..... Plt./224
See application file for complete search history.

(56) References Cited

U.S. PATENT DOCUMENTS

| | | | |
|---|---|---|---|
| PP11,119 | P | 11/1999 | Lamis |
| PP16,733 | P3 | 6/2006 | Baker, Sr. |
| PP19,807 | P2 | 3/2009 | Barbour et al. |

OTHER PUBLICATIONS

Gilman et al.; *Acer barbatum* (*saccharum*) var. caddo: Caddo Florida Maple; University of Florida, IFAS Extension ENH167; pp. 1-3; 2012.*

* cited by examiner

*Primary Examiner* — Kent L Bell
(74) *Attorney, Agent, or Firm* — Jeffrey L. Streets; Streets & Steele

(57) ABSTRACT

A variety of sugar maple, *Acer saccharum* var. *caddo*, named 'WHIT XLV', is characterized by an upright and oval growth habit at the age of 16 years, but is expected to develop a more rounded crown with age and may reach a height of 30 feet with a 25 foot spread. Leaves emerge medium green and quickly change to very dark glossy green. When adequate spring moisture is present, all leaves on the flush of growth develop full size. However, when spring moisture becomes limiting before all leaves on the twig are produced, the younger leaves will become progressively smaller in size yet the same shape and dark green color. No flowers have been produced on this tree by age 16 years. Fall color develops late in the fall after various species of trees have developed fall color and most of the leaves have fallen.

10 Drawing Sheets

Genus, species: *Acer saccharum* var. *caddo*.
Varietal denomination: 'WHIT XLV'.

BACKGROUND OF THE INVENTION

1. Field of the Invention

The present invention relates to a new and distinct variety or cultivar of the ornamental tree, *Acer saccharum*, subspecies commonly known as Caddo sugar maple.

2. Description of the Related Art

Sugar maple trees are native over a huge range of North America and have been admired in particular for their fall foliage color beginning with the earliest settlers. Sugar maple trees have been planted in a variety of landscape situations for shade, form, wind shelters but particularly for fall foliage colors. In the general area east of the Mississippi river and north of about the 35$^{th}$ parallel the tree grows well in a range of environmental conditions. However, west and south of this area due to the relentless winds, low humidity and drought, plus the tendency of the soils to be more alkaline, the tree survives, but appearance is poor. Leaves of the eastern sugar maple tend to tatter and tear at the margins due to the winds and by mid to late summer leaves typically suffer from moderate to severe scorch and chlorosis of leaf margins, such that fall color is rendered poor to non existent.

During one or more of the North American periods referred to as an ice-age, tree species native to northern latitudes were forced to migrate south. When the ice receded and conditions became more hospitable, seedlings were dispersed from existing trees and over eons of time, migrated back to northern habitats. There are numerous examples of existing remnant plants of a northern species that have adapted and continue to survive in southern microclimates. One example is the remnant populations of American basswood, *Tilia americana*, trees found in unique microclimates of what is referred to as the hill country in west-central Texas. Another example is the population of sugar maple trees that remained and evolved in the canyons of west-central Oklahoma and the Texas panhandle area. The native habitat of these remnant trees is primarily in the accumulated debris near the base of steep canyon walls. These trees have developed thick leathery leaves and greater tolerance to drought and drying winds and alkaline soils compared to eastern sugar maple. When seedlings are moved from the protected canyon environment and planted in open windswept and more drought prone locations, the trees continue to resist the tough environmental assault.

Growing the tree from seed is difficult and impractical except on a very limited scale. Viable seeds are produced only every few years and from a given seed lot, germination may range from none to rarely more than 20%. Further, among the germinated seeds, only a fraction grow to make desirable trees and at a growth rate sufficient to be practical for commercial nurseries.

U.S. Plant Pat. No. 11,119 disclose a sugar maple tree with thick leathery glossy deep green leaves with good resistance to leaf tatter that is common to sugar maple trees. U.S. Plant Pat. No. 16,733 disclose a sugar maple tree having brilliant and unique fall color presentation and an upright structure that develops into a full spreading crown. U.S. Plant Pat. No. 19,807 disclose a sugar maple tree characterized by consistent vibrant orange fall colors in hardiness zone 8, heat tolerance and vigorous growth rate. In 2003, a sugar maple of Caddo origin with dark green summer foliage and brilliant, red early fall color was introduced under the cultivar name 'John Pair'. However, this tree is substantially different in that it flowers and produces seeds and grows only about six to eight inches per year according to information released. Such slow growth reduces its acceptance by the nursery industry as well as anyone planting it in the landscape.

The new variety of sugar maple tree claimed herein, which has been given the cultivar name 'WHIT XLV' was selected from a block of Caddo sugar maple seedlings resulting from seed collected from a tree in Stillwater, Okla. in 1994. There are no records as to the source of the parent tree and the parent tree was destroyed during a storm in 1999. Interest in Caddo sugar maple trees is of long standing by plant enthusiasts. Beginning in 1973, seeds from Caddo sugar maple trees growing in their native habitat in southwest Oklahoma were collected and compared to seed collected from various trees in landscapes and parks around the state. Seedlings from the selected parent tree in Stillwater, Okla. consistently had greater vigor compared to seeds from other parents. Of the seeds collected in 1994, five seedlings stood out from the rest and were saved when all others were judged to be culls and destroyed. Among these five, one grew faster and was judged superior and in the 16 years of working with this tree, it has never failed to produce spectacular fall color and regardless of whether the fall was especially wet or extremely dry.

This new and distinct sugar maple variety has never flowered or produced seed even though there are other trees resulting from the same parent and other parents within range for pollination. Being sterile is an advantage relative to the litter of seeds as occurs from eastern sugar maple and assures that the tree will never become invasive or weedy in landscapes.

This new and distinct sugar maple has been asexually reproduced by rooting softwood or semi-hardwood cuttings during May 2005, 2006, 2007, 2008, 2009 and 2010 from the discovered tree and placed under intermittent mist in a greenhouse. However, rooting percentages are low, ranging from zero to 30% and resulting plants grow slowly. By contrast, when budded onto eastern sugar maple seedlings, resulting plants grow with acceptable vigor to be viable in the nursery industry and are consistent with characteristics of the parent tree. Based on research I conducted in central Oklahoma years ago, eastern sugar maple seedlings survive even under severe drought and exposure but by mid summer become ugly due to foliage damage. In one study leaf tatter and chlorosis developed on eastern sugar maple seedlings even when maintained throughout the growing season with adequate water. These studies suggest that the root system of eastern sugar maple is adapted to a much wider range than the foliage and that the leaf tatter and chlorosis often cited as a problem with eastern sugar maple is strictly a foliage phenomenon. Therefore, budding this new and distinct Caddo sugar maple cultivar 'WHIT XLV' onto eastern sugar maple seedlings provides a superior root system—top combination.

SUMMARY OF THE INVENTION

The tree of the present invention is a new and distinct variety of sugar maple, *Acer saccharum* var. *caddo*, which has been given the cultivar name 'WHIT XLV' and is characterized by an upright and oval growth habit at the age of 16 years. The discovered tree at age 26 years was 33 feet tall with a 28 foot spread.

Leaves of the plant emerge medium green and quickly change to very dark glossy green. When adequate spring moisture is present, all leaves on the flush of growth develop full size. However, when spring moisture becomes limiting before all leaves on the twig are produced, the younger leaves will become progressively smaller in size yet the same shape and dark green color. This appears to be a distinct response to drought conditions and may aid the trees survival.

No flowers have been produced on this tree even though at age 16 years, flower production should have occurred. Other seedlings grown from the same parent start producing flowers about age 6 or 7.

During the growing season, this new and unique cultivar of sugar maple remains very dark green, with thick foliage. Fall color develops late in the fall after various species of trees such as oaks, pecans, walnuts, hackberries and others have developed fall color and most of the leaves have fallen. The tree then stands out and the impression is that it is not likely to develop fall color at all. However, in North Central Oklahoma in late October or early November, very slowly, fall color begins. At first a few yellow and reddish leaves appear at the top of the tree, then fall color progresses downward until the entire tree is aglow. Then gradually, the leaves become more orange-red and remain this color for weeks. Even after hard freezes, the leaves retain fall color but slowly decrease in intensity. Some seasons, the tree still has significant and eye catching fall color in mid-December or later. Leaves remain on the tree all winter and are dropped only with the beginning of spring growth.

BRIEF DESCRIPTIONS OF THE DRAWINGS

DETAILED BOTANICAL DESCRIPTION

The following botanical description is of the new and distinct cultivar of sugar maple, *Acer saccharum* var. *caddo*, which was given the cultivar name 'WHIT XLV'.

Specific color designations set forth by number designations are in accordance with The Royal Horticultural Society Colour Chart (1966). General color recitations are consistent with ordinary American color terminology.

The sugar maple, 'WHIT XLV' has not been observed under all possible environmental conditions. It is to be understood that the phenotype may vary significantly with variations in environment such as soils, temperature, light intensity and length of day without difference in the genotype of the plant. The following botanical characteristics and observations are taken from the plant when grown under normal outdoor conditions in north central Oklahoma. Unless otherwise noted, the following description is of the discovered tree, about 16 years old, growing near Stillwater, Okla.

The plant:

*Type.*—Deciduous woody tree with single stem and dense branching.

*Classification.*—Sugar maple, *Acer saccharum* var. *caddo*.

*Growth habit.*—Upright and broadly oval. The tree is a moderate grower with moderate branching off the main stem, but dense twigs and foliage over the outer canopy.

*Origin.*—Selected from a block of Caddo sugar maple seedlings resulting from seed collected from a tree in Stillwater, Okla. in 1994.

*Propagation.*—Soft wood or semi-hardwood cuttings root with modest success, but growth of the resulting plants is extremely slow. However, when budded onto eastern sugar maple root stock, growth is good and consistent with characteristics of the discovered tree.

*Size and shape.*—The discovered tree is upright — oval currently about 18 feet tall and 12 feet wide, however, it has been pruned severely each season in research efforts studying asexual propagation from cuttings. Without this annual pruning, the tree would likely be about 25 feet tall and 15 to 18 feet wide. Based on growth habits of much older seedlings from the same parent and growing on the same property and soils, it is expected to develop a more rounded crown with age and maturity and may reach a height of 30 feet with a 25 foot spread.

*Hardiness.*—The tree, as well as other seedlings from the same parent, was exposed to −19 degrees F., the coldest temperature ever recorded for north central Oklahoma on Feb. 13, 2011 yet no damage to twigs, buds or stems occurred. The tree is hardy throughout USDA hardiness zone 5.

*Pests and disease.*—The foliage has not been affected by powdery mildew or other fungal or bacterial pathogens and has had only very minor damage from insects typically present in north central Oklahoma.

The flowers: No flowers have been produced on this tree. At age 16 years, flower production should have occurred. Other seedlings from the same parent and with the same growing conditions start producing flowers at age 7 or 8.

Figure 1:
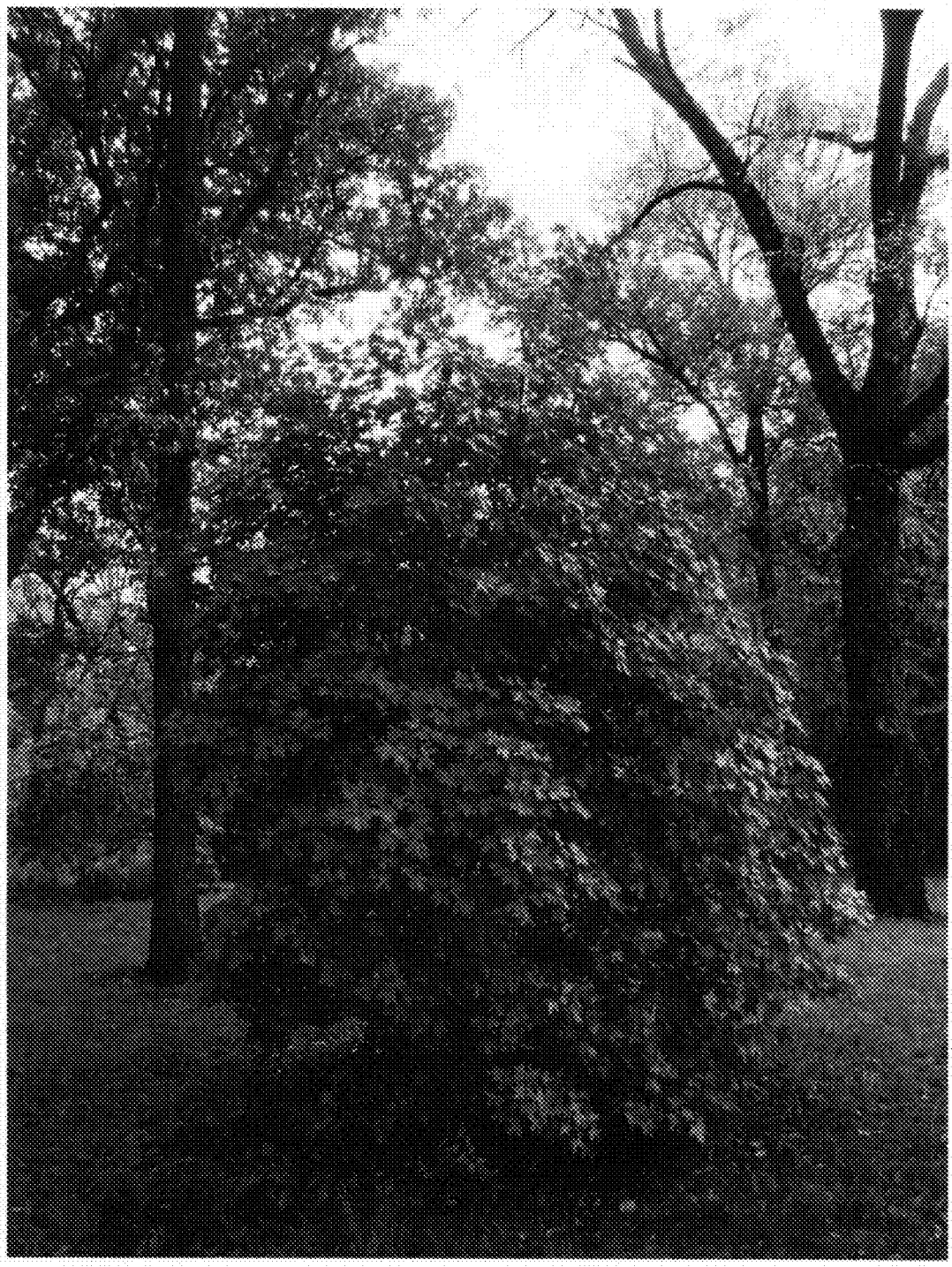
FIG. 1 is a full color photographic view of our new sugar maple tree 'WHIT XLV' showing the growth habit and dense dark green foliage in late September near Stillwater, Okla.
Figure 2:
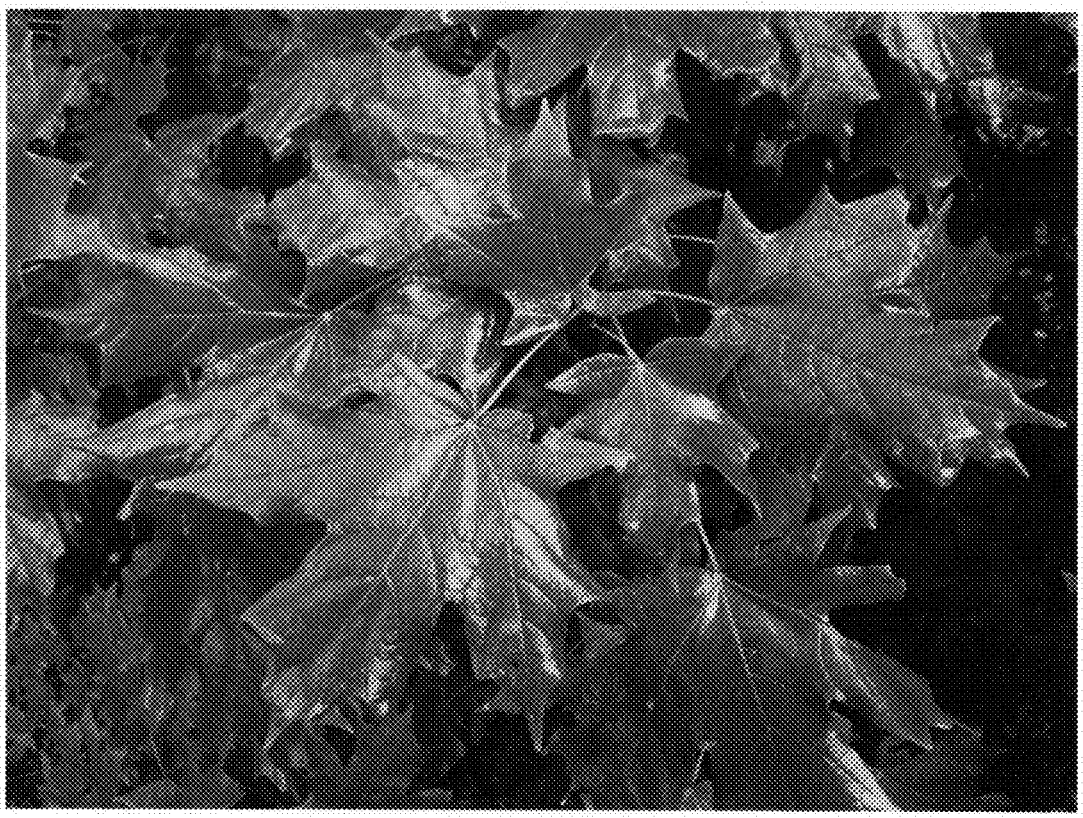
FIG. 2 is a full color photographic view of leaves of the new sugar maple tree in late September just after a rain that washed away dust and showing the dark green leaf color and with no tatter or leaf margin chlorosis.
Figure 3:
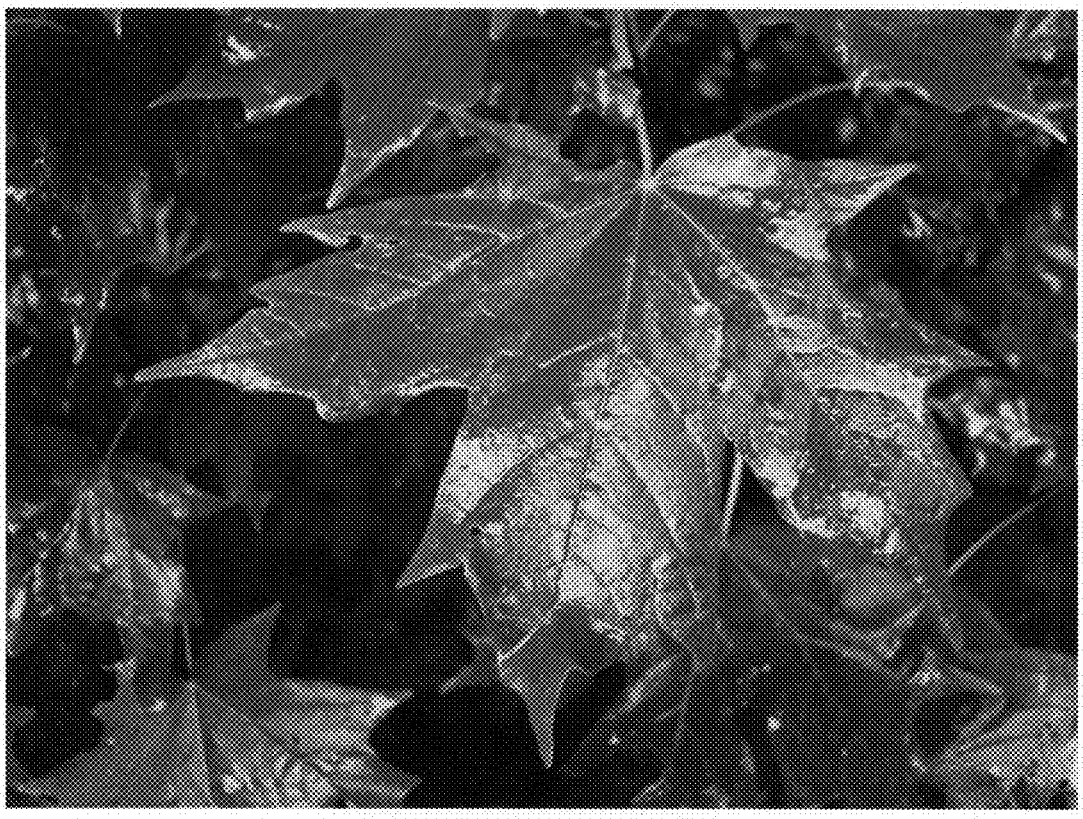
FIG. 3 is a full color photographic view of a single leaf still in excellent condition in late September following a rain that washed off dust.
Figure 4:
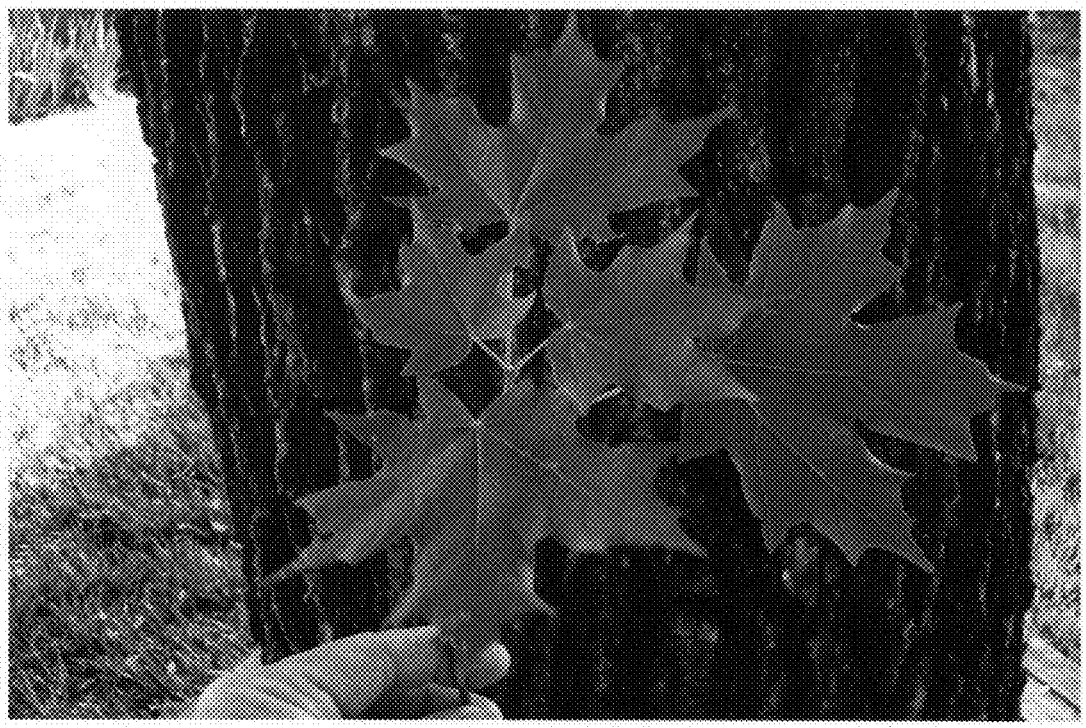
FIG. 4 is a full color photographic view of leaves produced on a twig during a spring with developing drought conditions. Note the oldest leaf at right, then the next oldest leaves at top and bottom that are smaller and the two even smaller leaves in the center.
Figure 5:
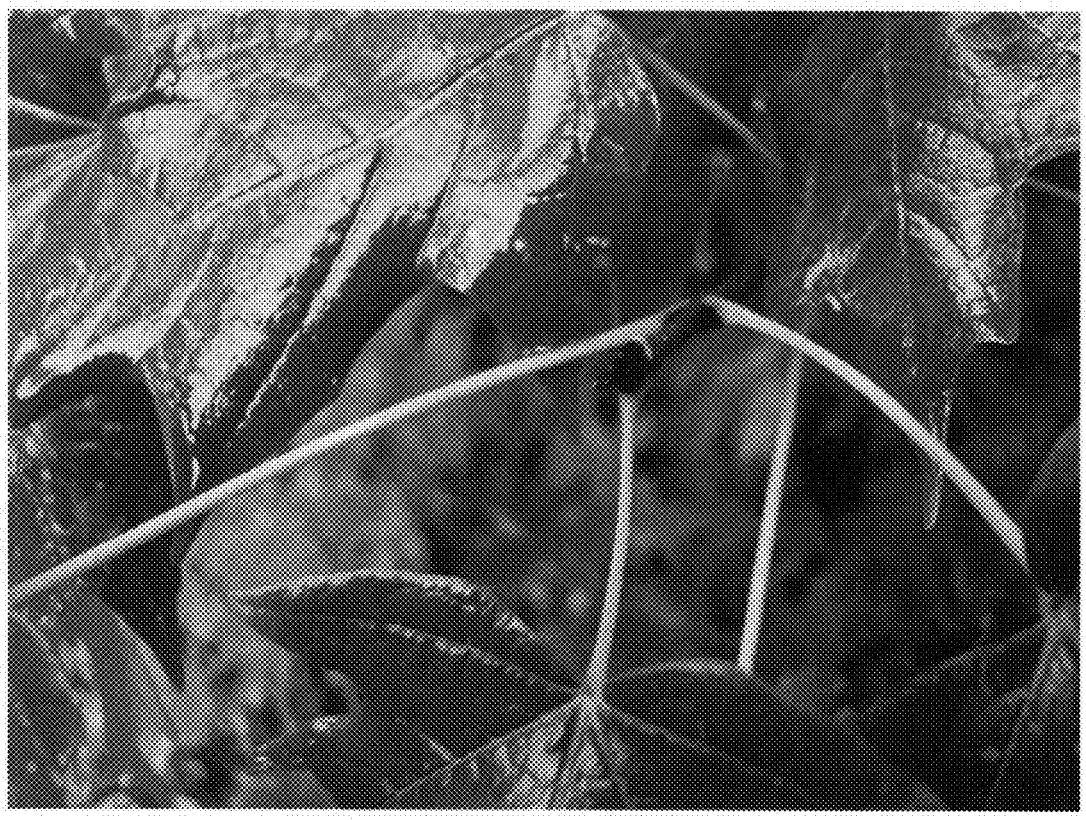
FIG. 5 is a full color photographic view of the terminal and axillary buds and maturing twig along with the slight pinkish color of the petioles.
Figure 6:
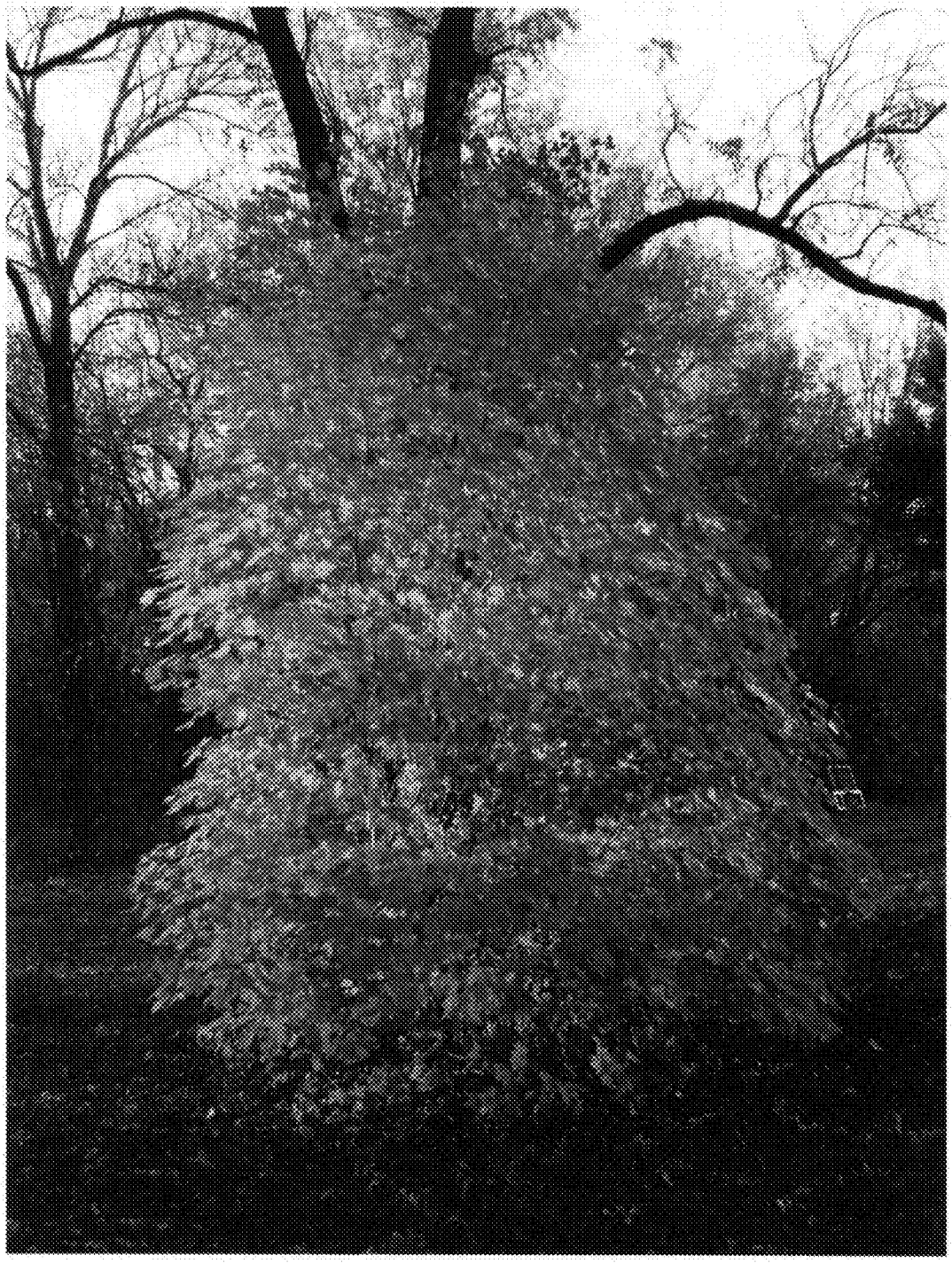
FIG. 6 is a full color photographic view of the tree in early stage of fall color development in early November in north central Oklahoma.
Figure 7:
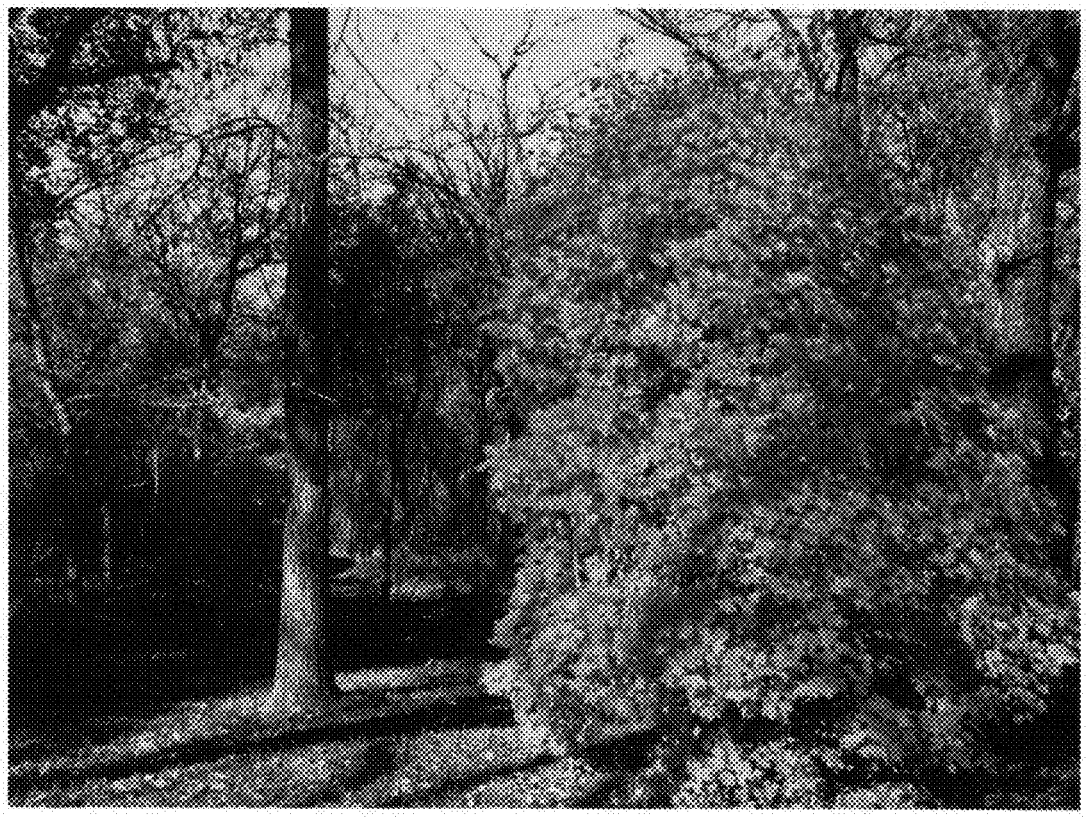
FIG. 7 is a full color photographic view of the tree in full fall color mode in mid-November in north central Oklahoma.
Figure 8:
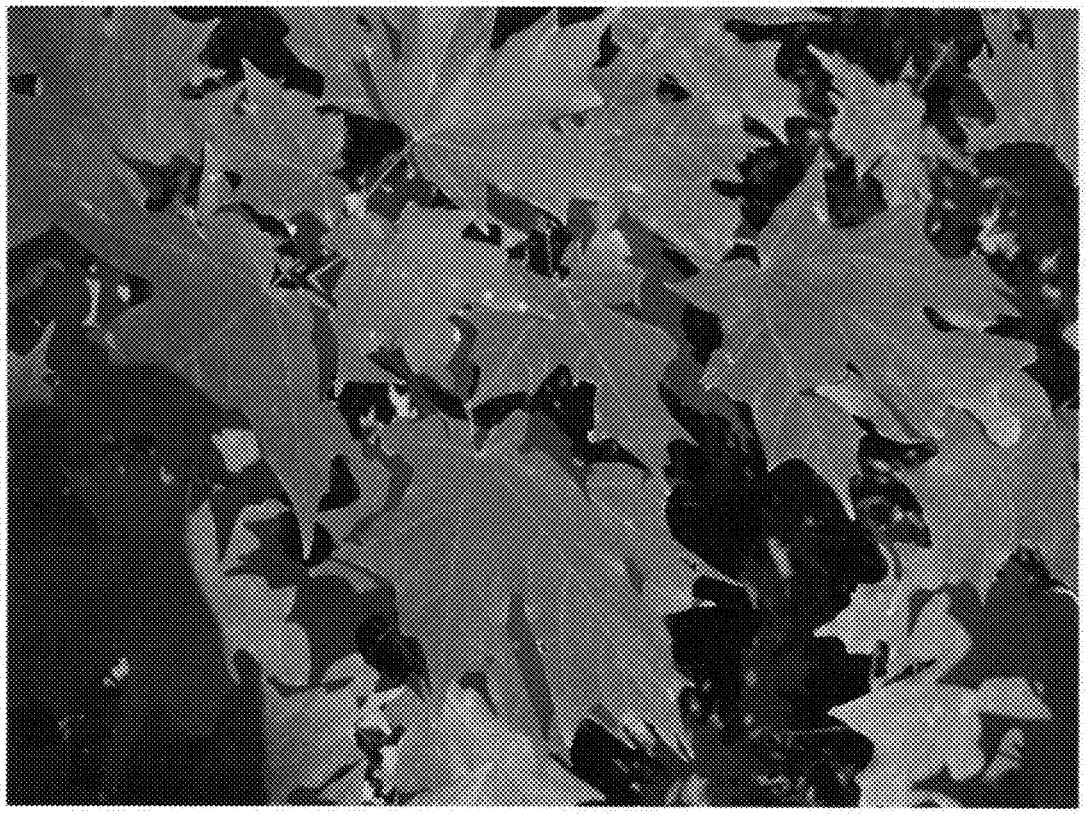
FIG. 8 is a full color photographic view of leaves on the tree shown in FIG. 7 in full fall color.
Figure 9:
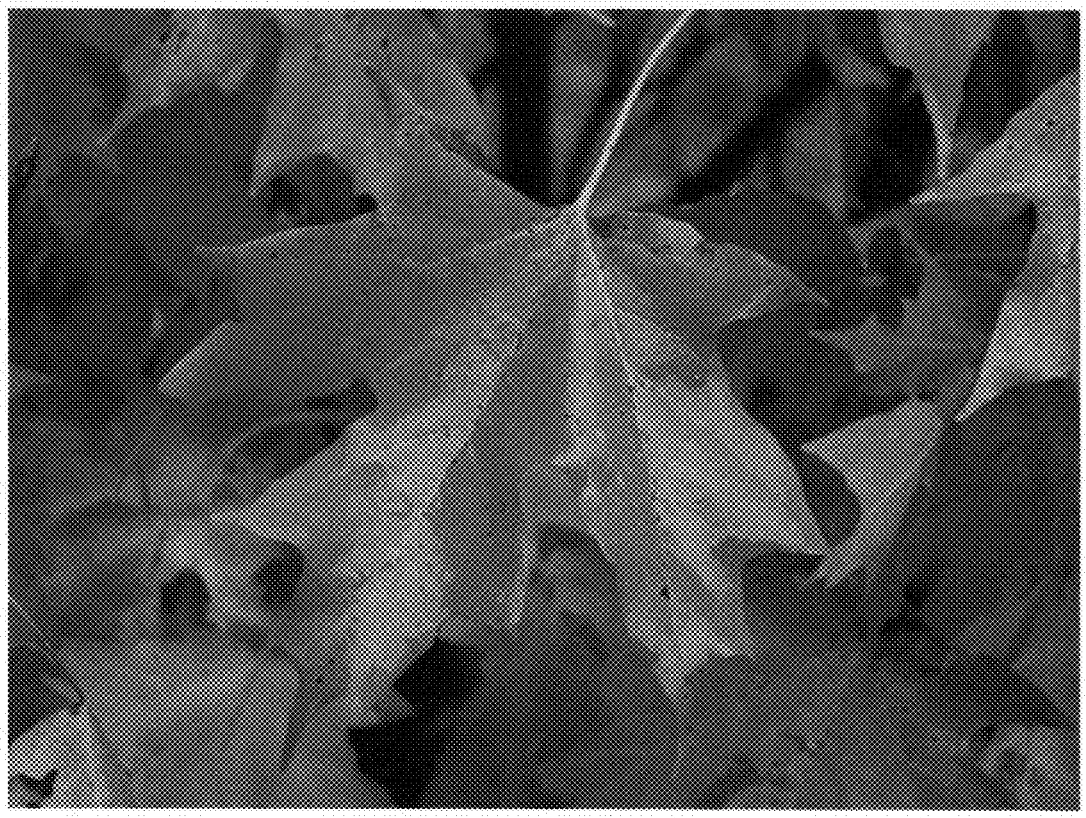
FIG. 9 is a full color photographic view of a leaf in full fall color showing leaf surface shine after a rain.

The foliage:

*Leaf shape.*—Simple, cordate to near orbicular in overall form, typically with 4 moderately deep sinuses, and 3 outer lobes much larger and distinct to the two smaller lobes near the base and from none to four small secondary lobes on the 3 primary lobes. Lobes are distinctly acuminate as shown in FIGS. 2, 3, and 4. Leaf base ranges from hastate to truncate to slightly cordate.

*Leaf size.*—Leaves are 2 to 4 inches across and 2 to 4 inches long, depending on moisture conditions during development as shown in FIG. 4. Leaf petioles typically range from ½ inch on leaves that developed during drought conditions and remain small, to 4 inches for leaves developed during adequate moisture.

*Leaf petiole.*—Petioles on leaves in shade or partial shade are cream colored, yellow-white group 158-B or 158-C, but outer leaves are typically red group 39-B, 39-C or 39-D depending on exposure.

*Leaf color.*—Upper surfaces of young leaves emerge medium green, green group 137-A and quickly change to dark green, green group 139-A, and remain so throughout the growing season until the onset of fall color. The underside of leaves is typically green group 137-A or 137-B. In late fall in north central Oklahoma and after other tree species have changed to fall color and most of their leaves have dropped the new sugar maple cultivar 'WHIT XLV' begins fall color. Fall color begins at the top of the tree, with the upper surfaces of a few leaves becoming yellow, yellow-orange group 20-A or 20-B, then slowly transitioning downward through orange-red group 34-A or 34-B, before reaching red group 53-B, 53-C or 53-D. The upper surface of all leaves eventually reach red group 53-B, 53-C or 53-D when dry, but appear as red-purple group 61-B or 61-C when damp with dew, frost or rain. Onset of fall color in north central Oklahoma typically begins in late October or early November and develops over a period of 12 to 18 days. Full fall color is retained for a period of 3 to 5 weeks, with a gradual fading of the intense reds and oranges with colder weather. However, leaves typically retain noticeable fall color well into December.

*Leaf texture.*—Mature leaves are glabrous on both upper and lower surfaces. There are three raised major leaf veins on the lower surface. Unlike eastern sugar maple, there is no pubescence on the lower leaf surface.

*Leaf retention.*—Leaves remain on the tree all winter. Leaf drop typically occurs only with the expansion of buds and new growth in the spring.

The branches and bark:

*Branch color.*—Immature current season stems are typically yellow-green group 144-A. One year old stems are typically greyed-orange group 165-A or 177-A or 177-B. Branches three years old are typically greyed-orange group 177-B or 177-C. The main stem and branches five years or older have no good match in the color chart, but are similar to greyed-green group 197-A or 197-B only darker.

*Branch length.*—Terminal growth is typically 16 inches during dry springs and up to 28 inches when moisture is plentiful. Branch length on side branches is typically from 6 to 12 inches.

*Branch diameter.*—Current season branches are typically about 1/8 inch in diameter, while second year branches are typically about 3/16 inch in diameter. Branches are moderately stiff and stout.

Figure 10:
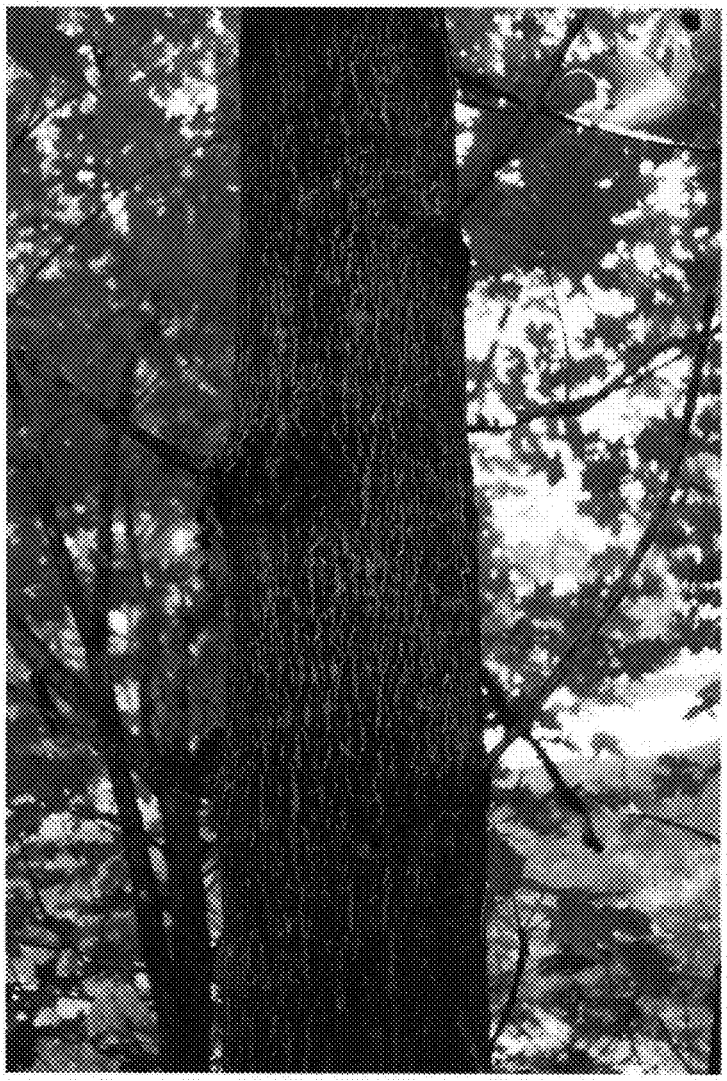
FIG. 10 is a full color photographic view of the main stem of the tree which is not unique or distinct and appears much like other sugar maple trees.

*Bark.*—Mature bark is grayish-black as shown in FIG. 10, but there are no good matches in The Royal Horticultural Society Colour Chart. At age 16 years, the base of the main stem shows no signs of exfoliating.

*Lenticels.*—Current season growth has lenticels having a length from 3/64 inch to 7/64 inch, arranged parallel with the long axis of the stem, and irregularly distributed both around the twig and along the vertical stem in no particular pattern. The lenticels have a width from 1/64 inch to 3/64 inch, and the lenticel color is greyed-orange group 164-A, 164-B or 164-C.

*Vegetative buds.*—Dormant vegetative terminal buds have a length from 1/32 inch to 14/32 inch. Auxiliary buds have a length from 3/32 inch to 5/32 inch. Dormant vegetative buds are brown group 200-B, 200-C or 200-D, and have from 9 to 15 bud scales showing.

I claim:

1. A new and distinct variety of sugar maple tree, substantially as illustrated and described.

* * * * *